US010318526B2

(12) United States Patent
Dean et al.

(10) Patent No.: US 10,318,526 B2
(45) Date of Patent: Jun. 11, 2019

(54) COMPLEX CHEMICAL SUBSTRUCTURE SEARCH QUERY BUILDING AND EXECUTION

(71) Applicant: Zymergen Inc., Emeryville, CA (US)

(72) Inventors: Jed Dean, Lafayette, CA (US); Adam Safir, Berkeley, CA (US); Gregory Michael Werner, Fremont, CA (US)

(73) Assignee: Zymergen Inc., Emeryville, CA (US)

( * ) Notice: Subject to any disclaimer, the term of this patent is extended or adjusted under 35 U.S.C. 154(b) by 512 days.

(21) Appl. No.: 15/202,439

(22) Filed: Jul. 5, 2016

(65) Prior Publication Data

US 2018/0011899 A1    Jan. 11, 2018

(51) Int. Cl.
| | | |
|---|---|---|
| *G06F 16/242* | (2019.01) | |
| *G06F 19/00* | (2018.01) | |
| *G06F 16/248* | (2019.01) | |
| *G06F 16/22* | (2019.01) | |
| *G06F 16/2455* | (2019.01) | |

(52) U.S. Cl.
CPC ...... *G06F 16/2428* (2019.01); *G06F 16/2246* (2019.01); *G06F 16/2282* (2019.01); *G06F 16/248* (2019.01); *G06F 16/2456* (2019.01); *G06F 19/709* (2013.01)

(58) Field of Classification Search
CPC ............. G06F 16/2456; G06F 16/2282; G06F 16/2246; G06F 16/248; G06F 16/2428; G06F 19/709
USPC ........................................................ 707/722
See application file for complete search history.

(56) References Cited

U.S. PATENT DOCUMENTS

| | | | | | |
|---|---|---|---|---|---|
| 4,811,217 | A | * | 3/1989 | Tokizane | G06F 19/705 707/758 |
| 5,421,008 | A | * | 5/1995 | Banning | G06F 16/2428 |
| 5,701,456 | A | * | 12/1997 | Jacopi | G06F 16/2428 |

(Continued)

FOREIGN PATENT DOCUMENTS

| | | |
|---|---|---|
| WO | 2005006216 A1 | 1/2005 |
| WO | WO 2005/017692 A2 * | 2/2005 |

OTHER PUBLICATIONS

Allen, Frank H., et al., "The Development of Versions 3 and 4 of the Cambridge Structural Database System", J. Chem. Inf. Comput. Sci., vol. 31, No. 2, © 1991, American Chemical Society, pp. 187-204.*

(Continued)

*Primary Examiner* — Robert Stevens
(74) *Attorney, Agent, or Firm* — Almanac IP Advisors LLP

(57) ABSTRACT

Systems and methods for enabling construction of complex Boolean chemical substructure queries in a structured graphical user interface are provided. The chemical substructures (molecules) may be represented graphically in standard molecular notation, and may be arranged horizontally and vertically on the interface, along with Boolean logical operators. Boolean logical operators of a first type may logically associate molecules arranged in horizontal fashion to form row queries, whereas Boolean logical operators of a different, second type may logically associate the row queries to form a composite query to be applied to a database of molecules. The operators of the first type may comprise disjunctive operators, whereas the operators of the second type may comprise conjunctive operators.

39 Claims, 9 Drawing Sheets

(56) References Cited

U.S. PATENT DOCUMENTS

| | | | |
|---|---|---|---|
| 7,250,950 | B2 | 7/2007 | Smith |
| 7,272,545 | B2* | 9/2007 | Phillips .................. C08G 77/00 |
| | | | 702/19 |
| 7,502,819 | B2 | 3/2009 | Alonso |
| 9,535,583 | B2* | 1/2017 | Smellie ............... G06F 3/04842 |
| 2002/0059297 | A1 | 5/2002 | Schirmer et al. |
| 2005/0004911 | A1* | 1/2005 | Goldberg ............ G06F 16/2428 |
| 2005/0039123 | A1* | 2/2005 | Kuchinsky .............. G06F 19/26 |
| | | | 715/205 |
| 2007/0112727 | A1 | 5/2007 | Jardine |
| 2009/0177455 | A1* | 7/2009 | Banerjee ............... G06F 19/708 |
| | | | 703/12 |
| 2012/0078853 | A1* | 3/2012 | Huang .................. G06F 16/245 |
| | | | 707/667 |
| 2013/0151572 | A1* | 6/2013 | Brocato ................ G06F 16/213 |
| | | | 707/805 |
| 2013/0218878 | A1* | 8/2013 | Smith .................. G06F 19/705 |
| | | | 707/723 |

OTHER PUBLICATIONS

Álvarez-Moreno, Moises, et al., "Managing the Computational Chemistry Big Data Problem: The ioChem-BD Platform", J. of Chem. Inf. Model., vol. 55, 2015, American Chemical Society, pp. 95-103.*

Bruno, Ian J., et al., "New Software for searching the Cambridge Structural Database and visualizing crystal structures", Acta Crystallographica Section B—Structural Science, © 2002 International Union of Crystallography, pp. 389-397.*

Cargill, John F., et al., "Object-relational databases: the next wave in pharmaceutical data management", Drug Discovery Today, vol. 3, No. 12, Dec. 1998, pp. 547-551.*

Anonymous: "jQuery QueryBuilder", Sep. 12, 2015, Retrieved from the Internet: <URL:http://web.archive.org/web/20150912195005/http://querybuilder.js.org/, 9 pgs.

International Application Serial No. PCT/US2017/040751, International Search Report dated Apr. 11, 2018, 3 pgs.

International Application Serial No. PCT/US2017/040751, Written Opinion dated Apr. 11, 2018, 8 pgs.

"Dynamic Chemical Substructure Search: Connecting Materials Science to Bioavailable Building Blocks," DARPA Final Report, DARPA Contract No. HR0011-14-0033, Defense Advanced Research Projects Agency, Microsystems Technology Office (MTO), submitted to DARPA Feb. 2015, 99 pages.

"Dynamic Chemical Substructure Search: Connecting Materials Science to Bioavailable Building Blocks," DARPA Proposal DARPA-BAA-12-64, submitted to DARPA Jul. 2, 2013, 11 pages.

A. Safir, "Dynamic Chemical Substructure Search: Connecting Materials Science to Bio-available Building Blocks," presented on Jun. 11, 2014 in meeting at DARPA, pp. 1-7.

J. Celko, "Binary Trees in SQL," redgate Hub, www.red-gate.com/simple-talk/sql/t-sql-programming/binary-trees-in-sql, Jun. 22, 2010, retrieved Aug. 11, 2017, 13 pages.

J. Barnard, "Chemical Structure Representation and Search Systems," Lecture 4, Nov. 11, 2003, pp. 1-47, Barnard Chemical Information Ltd., Sheffield, UK.

"Searching CrossFire Databases based on CrossFire Beilstein," CrossFire® Commander Version 7.1 Training Guide, May 2008, pp. 1-244 (see, e.g.,pp. 4-16, 5-2, 5-6, 5-7, 5-8), Elsevier Information Systems GmbH.

A.K. Yadav, "Data Structure Implementation to Query Binary Tree for Upline / Downline Node without using Recursion," Code Project, www.codeproject.com/Articles/124276/Data-Structure-Implementation-to-Query-Binary-Tree, Dec. 9, 2010, retrieved Aug. 11, 2017, 7 pages.

Ehrlich, et al., "Systematic benchmark of substructure search in molecular graphs—From Ullmann to VF2," Journal of Cheminformatics 2012, www.jcheminf.com/content/4/1/13, Jul. 31, 2012, 4:13, Chemistry Central, 17 pages.

E Lepekhin, "Trees in SQL databases" Sep. 22, 2004, Code Project, www.codeproject.com/Articles/8355/Trees-in-SQL-databases, 6 pages.

"How to Use Logical Operators in SQL Select Statement for MySQL," retrieved Dec. 29, 2017 from web.archive.org/web/20170620024509/http://www.geeksengine.com/database/basic-select/using-logical-operators.php, (Archived Jun. 20, 2017), 5 pages.

Edited by J. Gasteiger et al., Chemoinformatics (2003), title page, copyright page, and pp. 262-263, Wiley VCH GmBH & Co., Germany (excerpts from Google Books).

Hur et al., "PubChemSR: a search and retrieval tool for PubChem," Chem Cent J. 2008;2(1):11, 7 pages.

Kanehisa et al., "KEGG for integration and interpretation of large-scale molecular data sets," Nucleic Acids Res. 2012;40(Database issue):D109-14.

Krieger et al., "MetaCyc: a multiorganism database of metabolic pathways and enzymes," Nucleic Acids Res. 2004;32(Database issue):D438-42.

Spjuth et all, "Applications of the InChI in cheminformatics with the CDK and Bioclipse," J Cheminform. 2013;5(1):14 (7 pages).

O'Boyle et al., "Open Babel: An open chemical toolbox." J Cheminform. 2011;3(1):33 (14 pages).

\* cited by examiner (C1=CC=CC=C1 OR C1CCCCC1) AND C1CCC1 AND (C1C=CC=C1 OR C1CCCC1 OR C1CC1)

COMPLEX CHEMICAL SUBSTRUCTURE SEARCH QUERY BUILDING AND EXECUTION

STATEMENT REGARDING GOVERNMENT SUPPORT

This invention was made with Government support under prime contract HR0011-14-C-0033 awarded by DARPA. The Government has certain rights in the invention.

BACKGROUND

Chemists and material scientists advance their fields by using chemical building blocks in new ways. Access to catalogs of hundreds of thousands of candidate compounds enable creation of these new products. One such rapidly growing catalog of chemicals is made up of molecules found in biological systems, and which can be made accessible through synthetic biology. Many of these compounds would be extremely difficult and expensive to synthesize and purify using classic techniques of synthetic chemistry. However, poor search tools limit the usefulness of these growing biological repositories. The limitations of currently available search tools prevent scientists from rapidly identifying the building blocks that are of greatest utility, including those chemicals with biological origin contained in these newer repositories.

For example, the natural compound class of terpenes, thought to contain over 50,000 members, is practically impossible to search. No commercially available search tool is able to begin with this class of compounds, allow for development of a search statement targeting compounds with multiple substructures of interest (and substructures to exclude), and then return compounds that meet the criteria outlined. Instead, conventional commercial implementations contrive a way of reducing the tens of thousands of candidates down to hundreds using the selection criteria easiest to apply (e.g., molecular weight). Then each remaining candidate is evaluated and manually sorted, requiring substantial effort and thus imposing enormous costs for even minor tweaks to the search or sort criteria. These limitations mean lost time and opportunity as the best candidates may be missed and many inappropriate candidates offered up instead.

To optimize the use of new compound collections, new search tools are desired that would enable scientists to more easily construct queries that specify complex Boolean combinations of chemical substructures in a human-readable manner.

SUMMARY

Although the availability of enormous databases of chemical compounds provides a boon for chemists, existing computerized database systems give rise to technical problems in generating queries that chemists can feasibly generate to search those databases. Embodiments of the disclosure solve those problems by providing a structured graphical Boolean interface and translation techniques that enable the generation of complex queries through a graphical user interface that provides ease of use to chemists and others interested in developing new compounds based upon the enormous wealth of existing knowledge.

Embodiments of the disclosure provide systems and methods for enabling construction of a complex Boolean chemical substructure graphical query in a structured graphical user interface. The chemical substructures (molecules) may be represented using a standard molecular graphical model, and may be arranged horizontally in rows and vertically in at least one column of the interface. The molecules arranged in the rows may be associated with Boolean logical operators of a first type, also arranged horizontally, whereas the rows themselves may be associated with Boolean logical operators of a different, second type. The operators of the first type may comprise disjunctive operators such as OR and XOR, whereas the operators of the second type may comprise conjunctive operators such as AND and AND NOT.

In particular, a client-side user interface, or alternatively a server-side search engine, may receive data representing a Boolean combination of graphical representations of chemical substructures arranged in two or more rows of a graphical user interface. Associated with graphical representations of chemical substructures arranged in rows of the graphical user interface are logical operators, such as OR operators, representing logical combinations of a first type. Associated with at least two rows of the graphical user interface is at least one logical operator, such as an AND operator, representing at least one logical combination of a second type. In embodiments, client-side software may convert the graphical representations of the chemical substructures into non-graphical substructure representations, such as in SMILES format.

The following operations may be performed by client-side browser software or the server-side search engine, depending upon the embodiment. For each row having graphical substructure representations associated with at least one logical operator of a first type, combine each such first-type logical operator and its associated non-graphical substructure representations into a row sub-query, where each logical operator is associated with at most two non-graphical substructure representations in accordance with the Boolean combination. For each row, combine the row sub-queries into a row query in accordance with the Boolean combination. Combine the row queries with the at least one second-type logical operator in accordance with the Boolean combination to generate a composite search query.

The search engine executes the composite search query by applying the logical operators to the non-graphical substructure representations in accordance with the Boolean combination to produce Boolean query results comprising one or more chemical structures representing chemical compounds. The search engine may return the Boolean query results to the user interface for display.

In embodiments, if a row contains two or more two non-graphical chemical substructure representations, the row may be characterized as containing one or more unique pairs of non-graphical chemical substructure representations where each non-graphical chemical substructure representation may be a member of only one unique pair. In that case, combining each first-type logical operator and its associated non-graphical substructure representations into a row sub-query comprises: combining every adjacent unique pair of non-graphical chemical substructure representations in the row with its associated first-type logical operator to form a row sub-query for each pair; and combining any single uncombined non-graphical chemical substructure representation in the row with any uncombined first-type logical operator to form a row sub-query for the uncombined non-graphical chemical substructure representation.

In embodiments, each of the non-graphical representations resides in a tree data structure at an operand node that is related to at most one other operand node by a logical operator in accordance with the Boolean combination, and combining each first-type logical operator and its associated non-graphical representations into a row sub-query comprises combining each first-type logical operator and its related operand nodes into the row sub-query. The search engine may recursively traverse the tree data structure to generate a text-based database query to serve as the composite search query.

These and other embodiments are more fully described below.

DETAILED DESCRIPTION

The present description is made with reference to the accompanying drawings, in which various example embodiments are shown. However, many different example embodiments may be used, and thus the description should not be construed as limited to the example embodiments set forth herein. Rather, these example embodiments are provided so that this disclosure will be thorough and complete. Various modifications to the exemplary embodiments will be readily apparent to those skilled in the art, and the generic principles defined herein may be applied to other embodiments and applications without departing from the spirit and scope of the disclosure. Thus, this disclosure is not intended to be limited to the embodiments shown, but is to be accorded the widest scope consistent with the principles and features disclosed herein.

System Design

Figure 1:
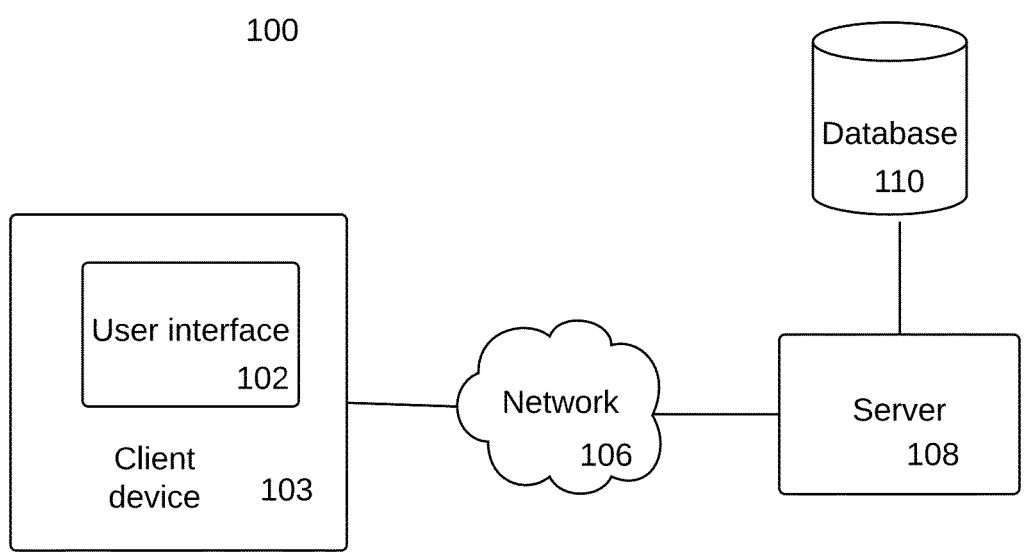
FIG. 1 illustrates a distributed search system of embodiments of the disclosure.

FIG. 1 illustrates a distributed search system 100 of embodiments of the disclosure. A user interface 102, such as a GUI in a web browser, includes a client-side drawing tool and a visual query editor. The user interface 102 may reside at a client-side computing device 103, such as a laptop or desktop computer. The client-side computing device 103 is coupled to one or more servers 108 through a network 106, such as the Internet. The server 108 includes a search engine 203 to translate the visual queries into standard database query form, such as SQL statements. The server 108 is coupled locally or remotely to one or more databases 110, which may include one or more corpora of molecule data. Databases 110 may include public databases such as PubChem, as well as custom databases generated by the user or others, e.g., databases including molecules generated via synthetic biology experiments performed by the user.

Figure 2:
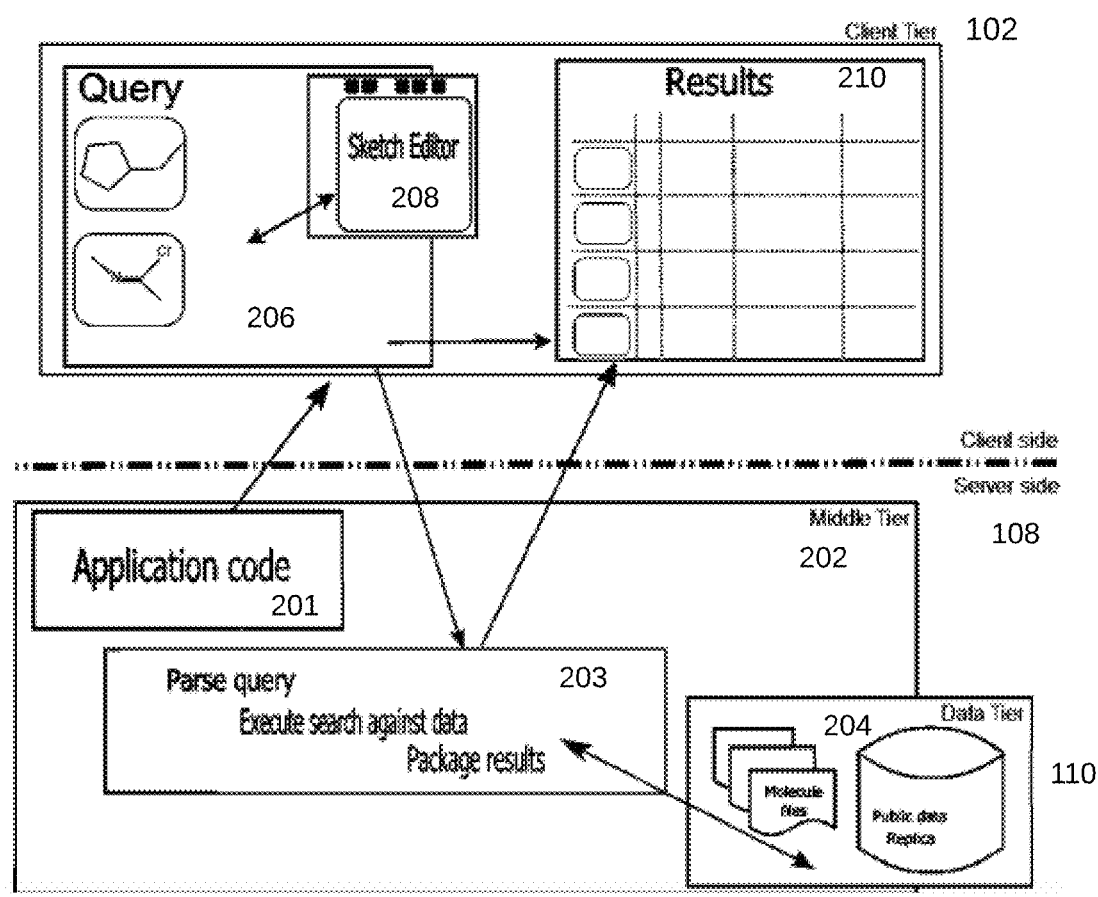
FIG. 2 illustrates portions of the system of FIG. 1 in more detail.

FIG. 2 illustrates parts of the system 100 of FIG. 1 in more detail. So that the search application may be easily run on different client operating systems without installation steps, embodiments employ a cloud application that runs in a web browser. On the client side user interface 102, the application provides interaction with end users using HTML pages with JavaScript. On the server side 108, in the cloud, the server 108 generates and filters data with web services.

Embodiments may be implemented in a hierarchy of N-tier applications. Referring to FIG. 2, the top level tier is the client-tier computing device 103, including web browser user interface 102 running HTML, CSS, and JavaScript code to interact with the end user. The top level tier obtains the code of the application 201 and the data requested by the end user using network requests to the middle tier 202 at the server 108. A search engine 203 at the middle tier 202 parses and interprets user requests, executes searches against one or more databases, and filters and orders search results. The middle tier 202 may be split into three or four independent services to preserve minimal coupling between pieces. The middle tier 202 may query databases managed by the data tier 204 on the database 110. The data tier 204 may reside within the same server 108 as the middle tier 202 or on a separate server.

The data tier 204 may employ a database 110 such as MySQL, MongoDB, or PostgreSQL. The database 110 stores each query molecule structure along with properties such as molecule names and mass. The molecules may be stored directly in a large text or binary field in the database. They may also be stored in separate files using known specialty chemical file format types, such as SMILES or SDF.

In addition, the database 110 may be used to collect statistical data about server usage. For example, query response times may be stored in the database for understanding performance limitations of the system and focusing future development efforts.

In embodiments, data from public resources such as PubChem, including molecule structures and properties, may be stored in the database 110. In this way public data may be mirrored in the data tier. Mirroring decouples the server side pieces from existing public services with the benefit that the system is then less dependent on a particular API. In addition, having data close to the middle tier 202 components provides more reliable performance. To mirror these public data repositories, scheduled tasks may keep the data up to date. These may be background processes that will not affect the end-user, and can be scheduled to run in off hours.

In addition to verbatim copies of public databases, the server enables the uploading of custom data sources. An example custom data set includes molecules generated by the user via synthetic biology. Custom data may be a subset of an existing public data set along with additional properties including private data generated during research experiments. The end user may specify which data set to query.

One task of the middle tier 202 components is to provide the application code 201 to run the application on the client web browser at the user interface 102. This is a fairly static task: each request to get the application results in basically the same chunks of HTML, CSS, and JavaScript code. The application may be separated into a few pieces matching each step of the application workflow—for example a query page 206 to combine query criteria, a sketch editor 208 to build chemistry-related criteria, and a browse results page 210 to navigate query results.

The search engine 203 at the middle tier 202 of the server 108 is mainly responsible for reading and interpreting client queries, executing client queries, and packaging query results back to the client. Query criteria involving primitive properties such as strings or numbers may be directly translated into database queries. Resulting record sets may then be filtered based on molecule criteria using chemistry-aware libraries. Query results may be packaged in text neutral strings, such as JSON or XML. The molecule structure may also be packaged in the same string. Alternatively, the middle tier 202 may provide an image url for each matching compound.

Substructure search on the middle tier 202 may be implemented in a number of ways. Some implementations hide the complexity of fingerprinting and subgraph isomorphism. One solution of this type is the open source Bingo GGA data cartridge, or if a MySQL database is employed, an alternative such as the RDKit database cartridge or MyChem may be employed. In embodiments, the search engine 203 employs the Bingo PostgreSQL cartridge to provide the core structure matching capabilities. Because this cartridge extends the capabilities of standard SQL, the search engine 203 is able to use all of the standard Boolean logic support in SQL. In other embodiments, the commercially available data cartridges may be combined with an additional chemical fingerprint library, or modified to use a custom chemical fingerprint library.

There are two main query operators with molecule structure: substructure and similarity filters. Compared to text search, the molecule substructure operator is comparable to the "contains" operator, and the molecule similarity operator is equivalent to a regular expression match.

For both similarity and substructure operators the criteria will take a partial molecular structure as argument. The partial molecular structure may be coded in different formats: SMILES, InChI, MOL, or Chemical Markup Language (CML). The value of the partial molecular structure argument will be compared to the molecular structure of each record in the data sources. Using indexing and other techniques the server avoids a full table scan to find matching records within acceptable waiting times. The substructure operator will find molecular structures fully containing the given partial molecular structure argument. This is equivalent of finding all graphs with a common subgraph.

The most computationally expensive task is to find the matching molecules for each criterion of the query. A molecule substructure search is a subgraph isomorphic operation. Time spent on this type of operation can increase exponentially as the subgraph and the target molecular structure grow bigger. There are known algorithms that improve subgraph isomorphism match: the Ullmann algorithm, the Schmidt and Druffel algorithm, the Nauty algorithm, and the VF2 algorithm (see Foggia et al. "A Performance Comparison of Five Algorithms for Graph Isomorphism," incorporated by reference herein in its entirety).

To further improve molecular structure selection (filtering), embodiments of the disclosure compute chemistry keys, or chemical fingerprints. Chemistry keys are a set of bits stating the presence or absence of well-known substructures (subgraph) within the full molecule structure (graph). They are computed when the molecule is added to the data source and indexed. The fingerprint keys are generated for public databases using known techniques, and may be generated for custom databases using the same or other known techniques. The PubChem database also uses a fingerprint index. Since PubChem is a large database and is currently in heavy use embodiments of the disclosure may mimic or use the same fingerprinting technique. The CACTVS Cheminformatics Toolkit enables this approach.

Other free open source implementations used to generate fingerprints are the Chemistry Development Toolkit, OpenBabel, and indigo Toolkit. The Indigo Toolkit has the advantage of sharing some source code with the Bingo relational database cartridge that can be installed with PostgreSQL. Database cartridges offer good integration of fingerprint generation and indexing, plus execution of subgraph isomorphism on records. The Bingo GGA molecular search engine is the foundation for the ChemSpider substructure search.

Substructure Query Search Implementation

To support the goal of allowing a user to interactively design a complex molecular substructure query, embodiments of the disclosure employ a number of data representations and translations. In embodiments, the query moves through several forms:

1) HTML text describing UI elements.
2) JavaScript objects defining how to create UI elements.
3) Binary tree defining Boolean logic query.
4) Tabular data representing the tree in database tables, e.g., SQL tables.
5) Actual query, in SQL or other similar, known database language, to be submitted to a substructure matching engine.
6) Lists of molecules that embody the results of user queries.
7) Filtered list based on user filter parameters.

Figure 3:
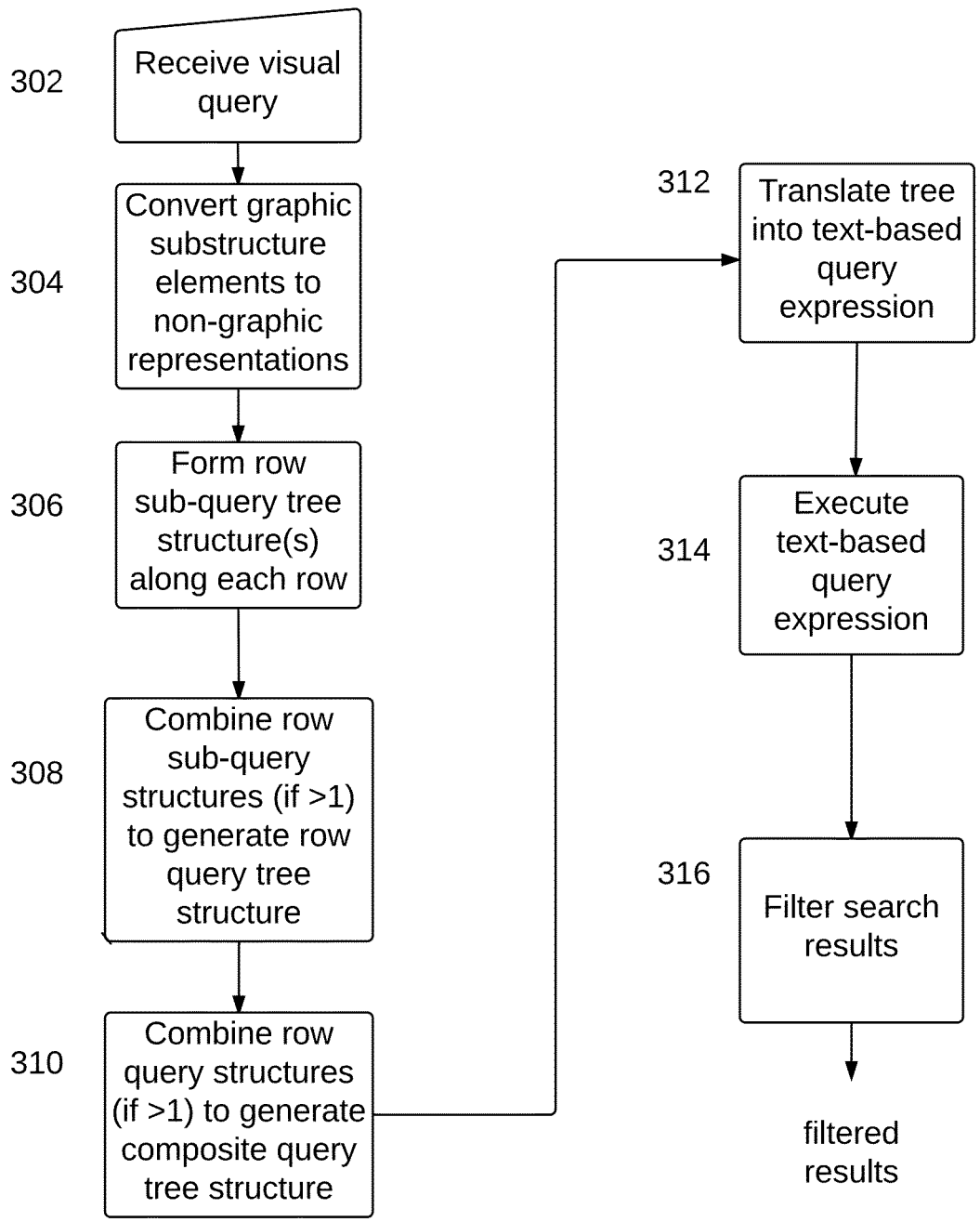
FIG. 3 is a flow chart illustrating query generation and execution according to embodiments of the disclosure.
Figure 4:
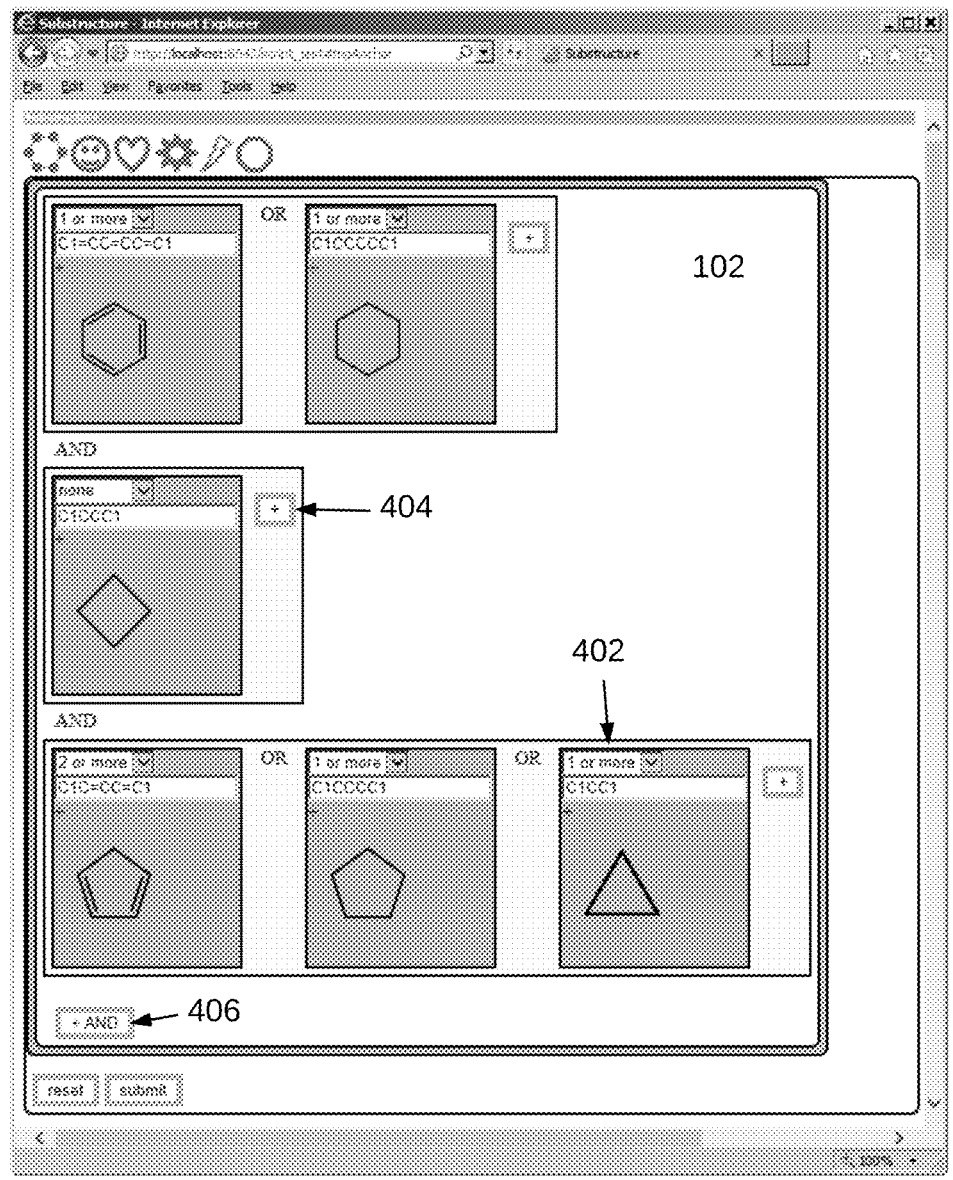
FIG. 4 illustrates an example graphical user interface of embodiments of the disclosure.

FIG. 3 is a flow chart illustrating query generation and execution, according to embodiments of the disclosure. FIG. 4 illustrates an example graphical user interface 102 of embodiments of the disclosure. Logical queries have complex syntax and are typically very difficult for people to write. The system of embodiments of the disclosure allows a user to specify an arbitrarily complex logical combination of molecular structures using visual tools and simple menus within an intuitive picture. To that end, the interface 102 is arranged as a graphical query form to receive substructures in rows and columns.

In this example, a user has drawn a graphical Boolean search query comprising graphical substructure elements (query terms) joined by logical operators (e.g., AND, OR). According to embodiments, the chemical substructures may be arranged horizontally in rows and vertically in columns of the interface. Boolean logical operators of a first type may be included in the rows on the display or otherwise associated with the substructures in a row, whereas Boolean logical operators of a different, second type may, for example, be interposed between the rows. Here, the operators of the first type may comprise disjunctive operators such as OR and XOR, whereas the operators of the second type may comprise conjunctive operators such as AND and AND NOT. Those skilled in the art would recognize that the types may be reversed in another embodiment.

A pull down menu associated with each term allows a numerical constraint (e.g., "1 or more", "2 or more", "none") such as constraint 402 (here "1 or more") to be added to each query term. These constraints are listed in simple human-readable form that specifies how many of a particular substructure needs to be present for a molecule to be considered a match. These numerical constraints may be expressed in language form, as shown, or with mathematical inequalities (e.g., =, <, >). In embodiments of the disclosure, the interface may employ the numerical constraint "none" in lieu of the "NOT" operator, thus eliminating the need for an "AND NOT" operator as a logical operator of the second type in such embodiments.

The software allows the user to interactively add diagrams (graphical query terms) to the diagram. Clicking the + button 404 at the end of a row allows the user to add an additional disjunctive term. Clicking the + button 406 at the bottom of the column allows the user to add an additional conjunctive expression.

By clicking on a particular diagram seen within the context of the whole query, the user can zoom in on that particular diagram to edit it. This allows an entire query to fit on a single viewable page while still providing a comfortable full screen editing experience for each individual diagram.

In an exemplary scenario, a representative from a client company defines the functional and economic requirements for a particular molecule, e.g., an electrical characteristic. Using extensive domain expertise, a chemist defines a set of chemical substructures (e.g., functional groups) that would likely be present or absent in a molecule that meets these requirements.

Substructure Query Input

In response, an operator/user inputs the chemical substructures into the query form on user interface 102. A molecule sketch editor 208 receives chemical substructures drawn by the user (302) (Parenthetical numbers beginning with the digit "3" refer to the process of FIG. 3). The editor 208 may be implemented on the client side with the JavaScript Ketcher tool running within the query form page 206 of the browser.

As the user interacts with the query building web page, the client computer 103 creates an in-browser-memory data structure of the page that represents everything that is visible to the user—pictures, buttons, pull down menus, and items selected within user interface elements. This data structure represents the page well, but is not directly useful to generate a database query, so undergoes several translation steps.

The Ketcher tool within the browser on the client side translates each drawn structure into one of three representations as needed—a textual, non-graphical representation (e.g., SMILES) for database storage and query generation (304), a PNG image for compact viewing within a query, and an object-oriented data object for use within the molecular structure drawing tool.

Binary Tree Formation

In embodiments, the browser and client computer 103 may convert the graphical query into a Boolean tree in JavaScript (306-310), and send the completed tree data structure to the search engine 203 for further processing.

In alternative embodiments, instead of the client-side computing device creating the tree data structure, the client-side computing device 103 sends over the network 106 to the search engine 203 the in-browser-memory data structure representing the user interface page. In such embodiments, the search engine 203 on the server side 108 uses the information from page data structure to convert the graphical query on the query page into a Boolean tree (306-310), and performs further translations to create the final query that is run against the database 110 in the data tier 204.

Figure 5:
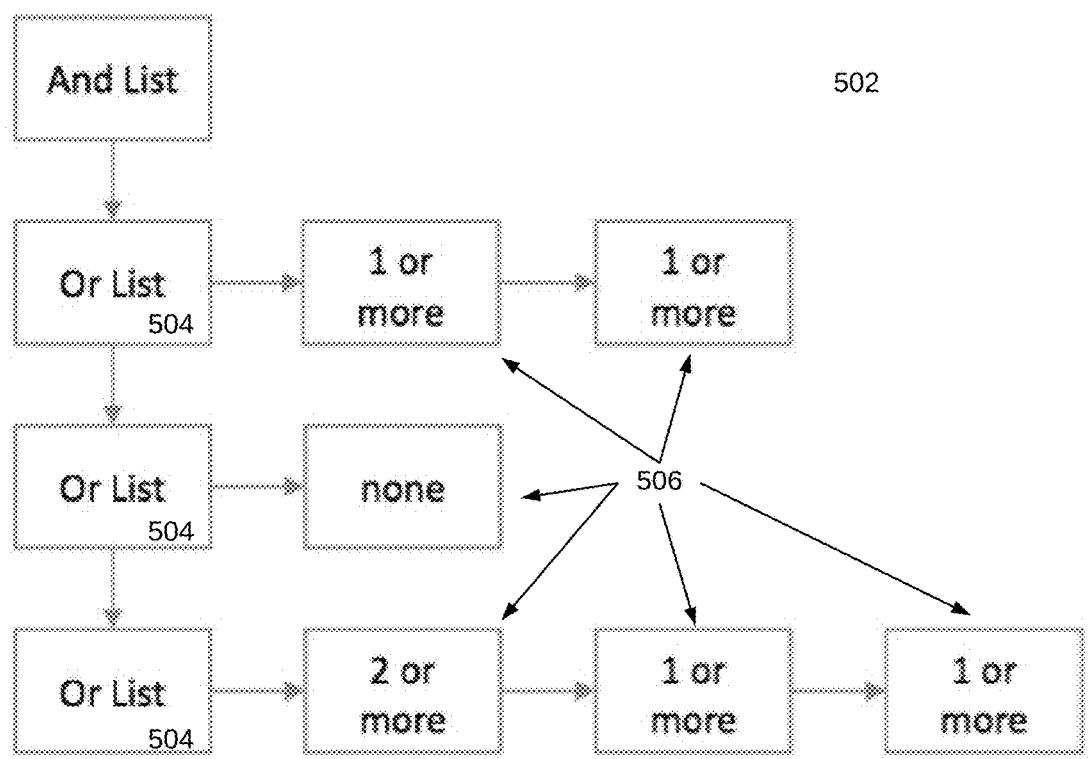
FIG. 5 illustrates a generic Python data tree structure of embodiments of the disclosure.

Referring to FIG. 5, in embodiments where the search engine 203 on the server generates the tree data structure, it may form a Python list of lists. An overall list 502 contains, for each row, a list of molecules with their associated logical operators 504 and constraints 506.

The discussion that follows assumes that the client-side computing device 103 and browser software creates the tree data structure in, e.g., JavaScript, although, in other embodiments, server-side software (e.g., search engine 203) may instead perform that function.

Assuming client-side tree formation, using the information from the in-browser memory data structure for the query page the browser software converts the graphical query on the query page into a Boolean tree (306-310) where each internal node in the tree represents a Boolean operation (AND, OR, XOR, NOT) from the query page, and each leaf node on the tree represents a molecular substructure from the query page, defined as a text-formatted (e.g., SMILES-formatted) chemical definition string, along with the numerical constraint from the query page associated with that substructure term.

The browser software need not make any assumptions about the number of terms in the Boolean expression, and their relationships, that might be produced by the web interface. It is flexible in parsing the data posted by the web interface. To do so, in embodiments, the browser software iteratively creates a JavaScript data structure. The data structure, in one example, includes SMILES textual representations of the molecules of the Boolean query, a representation of the logical operators and their relationships to the molecular textual representations along with the numerical constraint information.

More particularly, in this example the browser software parses the rows and columns of the HTML query page (with the substructures represented by the SMILES molecule elements) into a tree data structure, as follows:

Substructure molecules: Place each molecule into a tree leaf node.

Logical operators: Place each logical operator into a tree node, and associate each logical operator with at most two child nodes. The child nodes may comprise at most two molecule nodes, at most two other logical operator nodes, or a combination of one molecule node and one logical operator node.

If a child node comprises one or more logical operators, subtrees are recursively generated for each logical operator until the recursion encounters no further logical operator child nodes (i.e., only one or two molecule child nodes remain).

In embodiments, the browser software may traverse the data structure representing the HTML page in a left-to-right fashion starting at, for example, the upper left of the screen interface. Referring to the graphical query page of FIG. 4, in embodiments the browser software acts on a row-by-row basis to generate the Boolean tree data structure of FIG. 6 (which may be implemented in JavaScript in client-side tree formation embodiments, and in Python in server-side tree formation embodiments, as shown in FIG. 5).

In general, the query tree structure is formed according to the following process:

The browser software at the client computing device 103 parses the HTML and its XML representation to create an in-memory Javascript tree data structure, and converts that data structure into a textual representation that can be transmitted to the server 108.

The steps for the conversion from an HTML representation to a Javascript data structure follow.

The XML DOM (Document Object Model) structure for the page is retrieved using a JavaScript function call to the browser.

This XML is then parsed by iteratively moving through sections that represent the query grid.

First, the HTML DIV section of the web page that contains the query is extracted.

Next, the DIV containing each row from the query DIV is extracted. For each row the following process is completed:

The DIV containing each column within each row is extracted. For each column, the following process is completed:

Variables containing textual representations of the substructure for a particular row and column are identified.

The HTML menu containing the numerical constraint for the substructure is identified and its selected value determined.

Unless the substructure is the first in the row, the HTML menu containing the Boolean operation associated with the substructure is identified and its state determined to identify what operation was selected. The first substructure does not have an associated Boolean operation.

A new substructure tree node is created which contains the substructure representation along with variables that contain numerical constraints.

A separate Boolean tree node is created for the operator, if present.

The Boolean tree node, if present, is assigned to be the parent of the substructure node.

The Boolean tree node is assigned to also be the parent of the previously created Boolean tree node for this row, if one exists. At this point, the new Boolean tree node is the root of the tree representing all of the columns processed so far in this row.

This completes the per-column processing for a given row.

For any row beyond the first, a new Boolean tree node (typically representing AND) is created, and is assigned to be the parent node for the just completed row subtree and the subtree containing all previously processed rows.

This completes the per-row processing.

Figure 6:
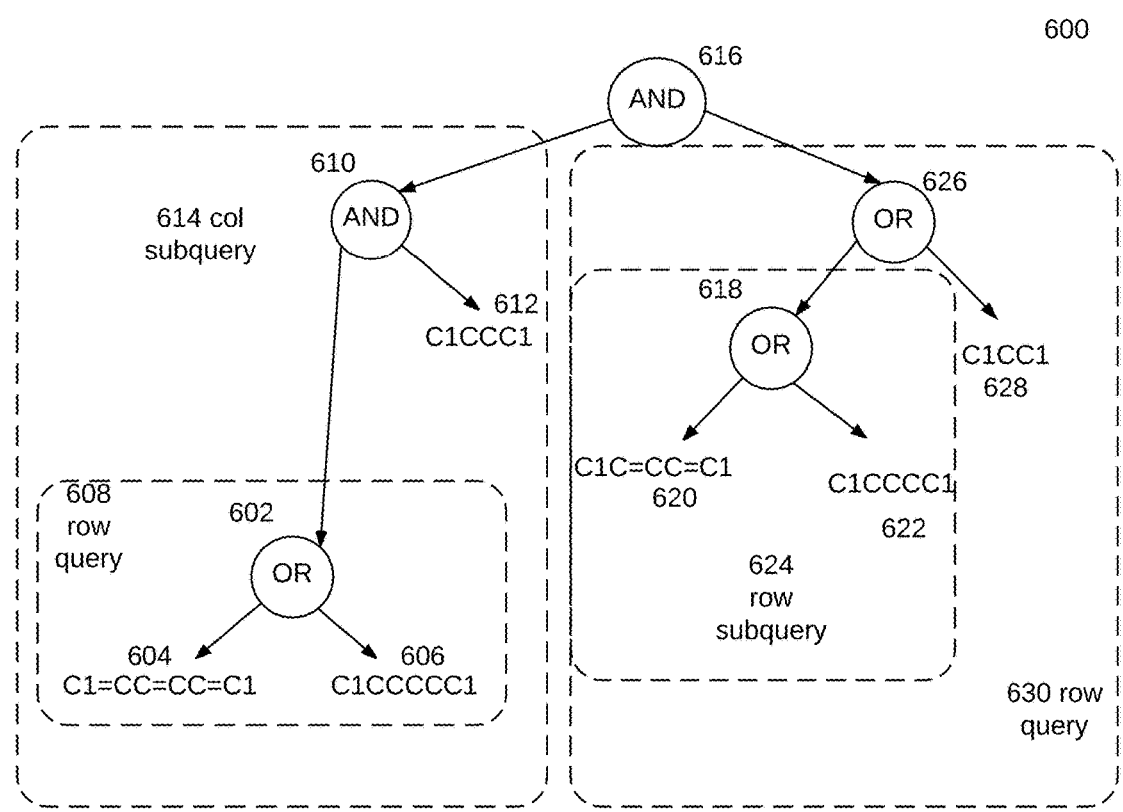
FIG. 6 illustrate an example tree data structure representing a Boolean substructure query according to embodiments of the disclosure.

An example of query tree structure generation follows, with reference to FIG. 6. Starting with the top row, the browser software places the first logical operator it encounters (OR) into a node 602 (denoted here a "logical operator node") and places the immediately adjacent left and right molecules (C1=CC=CC=C1; C1CCCCC1) into two child nodes 604, 606, respectively, of that logical operator node 602 to form a first row sub-query tree structure 608 (represented for convenience here in text form as C1=CC=CC=C1 OR C1CCCCC1; actually represented as a data structure in JavaScript, Python or other language in some embodiments) (306). Because the row includes no other logical operators, the row sub-query structure 608 serves as a row query structure 608 for the row. If this row included more than one logical operator (which is not the case here), then the browser software would combine the multiple row sub-query structures into a row query structure (308).

In this example, the browser software vertically steps down the in-browser-memory data structure representing the web interface page and encounters, for the first time, the logical operator AND. In embodiments, the browser software places the AND operator into a node 610, and adds the first row query structure 608, C1=CC=CC=C1 OR C1CCCCC1, as the left child node of the AND operator node 610. The browser software steps down to the second row and encounters the C1CCC1 molecule and inserts it into a node 612. (Note that because the second row includes no logical operators, the browser software does not need to further evaluate the row, and treats node 612 as the row query structure for the second row.) The browser software adds the C1CCC1 node 612 as the right child node of the first AND operator node 610 to thereby combine the row query tree structures of the first and second rows to form the cumulative, column sub-query structure 614, (C1=CC=CC=C1 OR C1CCCCC1) AND C1CCC1 (310).

The browser software again steps vertically down the memory structure representing the web query form and encounters a second AND logical operator. In embodiments, the browser software places this AND into a node 616. Because the second AND is the last operator encountered vertically, the browser software makes node 616 the root node of the tree. The browser software adds the current cumulative, column sub-query structure 614, (C1=CC=CC=C1 OR C1CCCCC1) AND C1CCC1, as the left child node of the second AND operator node 616, and then proceeds to generate the row query stricture for the following row.

For the third row, the browser software continues to generate the tree structure by again traversing the query form memory structure left to right. The browser software places the first logical operator it encounters in the row (OR) into a node 618, and places the immediately adjacent left and right molecules (C1C=CC=C1; C1CCCC1) into two child nodes 620, 622, respectively, of that first OR node 618 in the row to form the first row sub-query structure for the third row 624, C1C=CC=C1 OR C1CCCC1 (306).

The browser software next encounters a second OR in the row and places it into a node 626. The browser software adds the row sub-query structure 624, C1C=CC=C1 OR C1CCCC1, as the left child node of the OR node 626. The browser software places the C1CC1 molecule from the web page memory structure into a node 628 as the right child node of the OR node 626 to form OR C1CC1 (626, 628) as the second row sub-query structure for the third row (306), thereby also forming the row query structure 630, C1C=CC=C1 OR C1CCCC1 OR C1CC1, for the third row (308). The browser software adds the row query structure 630 as the right child node of the root AND node 616. As a result, the browser software forms the resulting, composite query structural expression 600: (C1=CC=CC=C1 OR C1CCCCC1) AND C1CCC1 AND (C1C=CC=C1 OR C1CCCC1 OR C1CC1) (310). As noted above, the browser software may represent this tree structure in a JavaScript data structure in embodiments of the disclosure. Alternatively, if the search engine forms the tree, then it may represent the tree structure in Python form.

In the embodiment just described the browser software adds row query structures as children of the AND operator nodes as the browser software traverses the web page query form data structure from left to right, top to bottom. Alternatively, the browser software may first form the row sub-query structures without combining them, and then combine them all at once, or piecewise, to generate the row query structures, and then combine those all at once, or piecewise, to generate the composite query structure. For example, FIG. 3 may be interpreted as showing, in one embodiment, formation of the row sub-query tree structures along all rows first (306), followed by combination of the row sub-query tree structures within each row to generate a row query structure for each row (308), followed by combination of all row query structures to form the composite query structure (310).

Query Tree Translation

Trees cannot be stored natively in standard databases such as text-based databases such as SQL databases. After the user's query has been translated from web query form data into the Boolean tree data structure in, e.g., JavaScript or Python format, it is translated a second time into a query in a text-based database format, e.g., SQL (312). In embodiments in which the client-side browser software forms the tree structure, the client device 103 sends the query tree data structure to the server 103 for further processing, as described below. In embodiments in which the server-side search engine 203 forms the tree data structure, the search engine 203 continues with the further processing described below.

The search engine 203 traverses the tree structure one node at a time and converts each node into a text form that can be stored using text-based database languages such as standard SQL. The search engine 203 may optionally place the molecule nodes in a first database table, the numerical constraint nodes (e.g., "not more than 2," "more than 1," "3,") in a second database table, and the relationships among the nodes in a join table. As described below, this stored information may later be retrieved to form a query template for future queries.

To translate the molecule/logical operator portion of the tree into SQL, the search engine 203 performs an in-order recursive traversal, starting at the root AND logical operator node 616, according to embodiments of the disclosure. At each internal (non-leaf, logical operator) node, the search engine 203 first visits the left child node, evaluates that left child node, and then visits the right child node to evaluate it. The search engine 203, however, does not perform the actual translation of a child until its left child and all the left child's descendants have been evaluated. In this manner, translation is deferred until the algorithm pushes down through the tree and reaches a leaf node. The algorithm then moves back up the tree to sequentially evaluate the ancestors of that leaf node, and then visits the right child node and evaluates it in the same manner, before finally translating all the nodes.

The general approach may be represented by the function below, which is originally called for the root node of the tree.
function translate(node):
   if there is a left child:
     1. write out some SQL query text
     recursively call translate(left child)
     actually translate the node
     2. write out some SQL query text
   if there is a right child:
     3. write out some SQL query text
     recursively call translate(right child)
     4. write out some SQL query text During this in-order recursive traversal of the tree, text is emitted to create a query. During the evaluation of every node, query text is emitted several times:
before the recursive call to the node's first child;
after the recursive call to the node's first child;
before the recursive call to the node's second child; and
after the recursive call to the node's second child.

By emitting the appropriate text during parsing, a SQL query can be generated. For example, during the translation of the binary tree in FIG. 6, the following text is written out at specified locations in the translate function for particular nodes.

For the root node of the query (616), the text emissions in SQL format may be of the form:
1. "Select * from bingo.pubchem where"
2. "("
3. ") AND ("
4. ") order by id"

For a typical substructure node (604), the text emissions may be of the form:
1. Nothing
2. molecules @ ('C1=CC=CC=C1,')::bingo.sub
3. Nothing
4. Nothing For a typical Boolean operator node (602), the text emissions may be of the form:
1. Nothing
2. "("
3. ") OR ("
4. ")"

Note that generation of the Boolean tree structure is not limited to the in-order recursive tree traversal algorithm of this embodiment, but may in other embodiments be performed using other tree traversal algorithms applied to the Boolean query tree structure.

After the tree has been fully translated into SQL, the search engine 203 executes the SQL query against the database 204 to return a set of molecules as search results (314). The search engine 203 sends the results over the network 106 to the results page 210 at the client. At that point, the user may filter the search results based on parameters such as melting point (316).

Translating Numerical Constraints

Numerical constraints introduce significant complexity to the translation because they cannot be translated directly into SQL. The Bingo engine and similar cheminformatics engines only allow for matching the presence or absence of a pattern. Converting numerical constraints requires dividing the main query into multiple queries whose results are combined with set operations.

For example, if the query entry page specifies a query to find a molecule with exactly N copies of a particular sub-structure "X", in embodiments the search engine 203 may convert that query into text-based (e.g., SQL) queries to:

1) find molecules with at least N copies of X, e.g., find molecules with X AND X AND . . . AND X (with X repeated N times). This result will include molecules with N or more Xs.

2) find molecules with at least N+1 copies of X, e.g., find molecules with X AND X AND . . . AND X (with X repeated N+1 times). This result will include molecules with N+1 or more Xs.

Then using set operations, the search engine 203 removes all results from query 2 above from the results of query 1. This leaves only molecules with exactly N copies of the desired sub-structure. These can be retrieved using the limited querying ability of the matching (e.g., SQL) engine.

Complex Substructure Query Example

Figure 7:
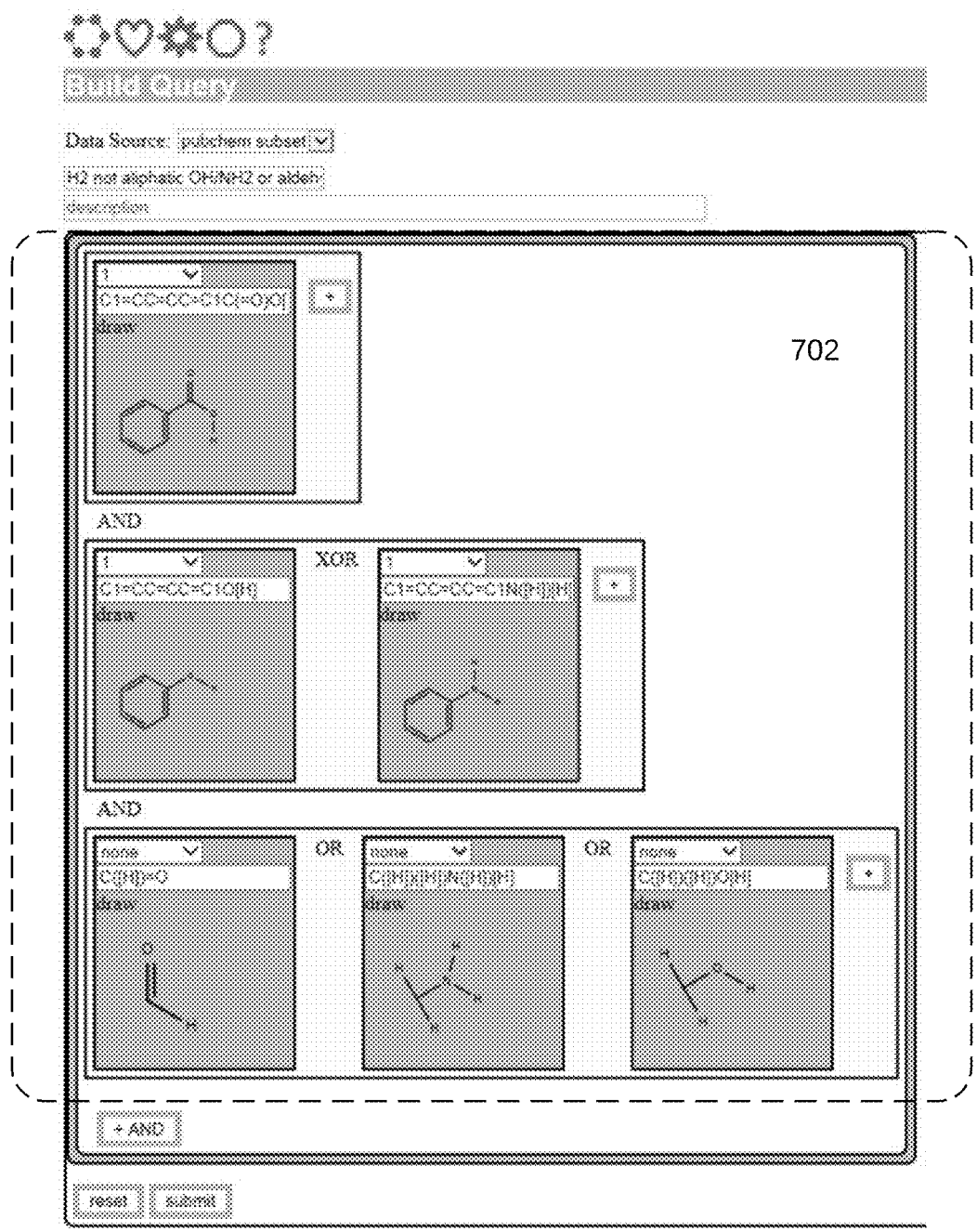
FIG. 7 illustrates a graphical user interface including an example complex graphical substructure query entered into the query page according to embodiments of the disclosure.

FIG. 7 particularly illustrates the complexity of the queries that can be generated using the query generator of embodiments of the disclosure. The query "aromatic acid OH/NH2 not aliphatic OH/NH2 or aldehyde" 702 graphically entered into the query page of FIG. 7 is an example of how one may search for building blocks for high performance polyesters and polyamines. One way to construct such polymers is to combine both reactive groups into a single molecular species. Specifically, for polyesters this means the molecule must have one aromatic carboxylic acid and one aromatic alcohol, while for polyamides one would need molecules containing one aromatic acid and one aromatic primary amine. In addition there are various other functional groups which could cause unwanted side reactions during polymerization; some examples of these are aldehydes, aliphatic alcohols, and aliphatic primary amines.

For a human user to combine all these attributes into a single search would be extraordinarily difficult. Although the availability of enormous databases of chemical compounds provides a boon for chemists, existing computerized database systems give rise to technical problems in generating queries that chemists can feasibly generate to search those databases. Embodiments of the disclosure solve those problems by providing a structured graphical Boolean interface and translation techniques that enable the generation of complex queries through a graphical user interface surprisingly simple to use, as illustrated in FIG. 7.

Figure 8:
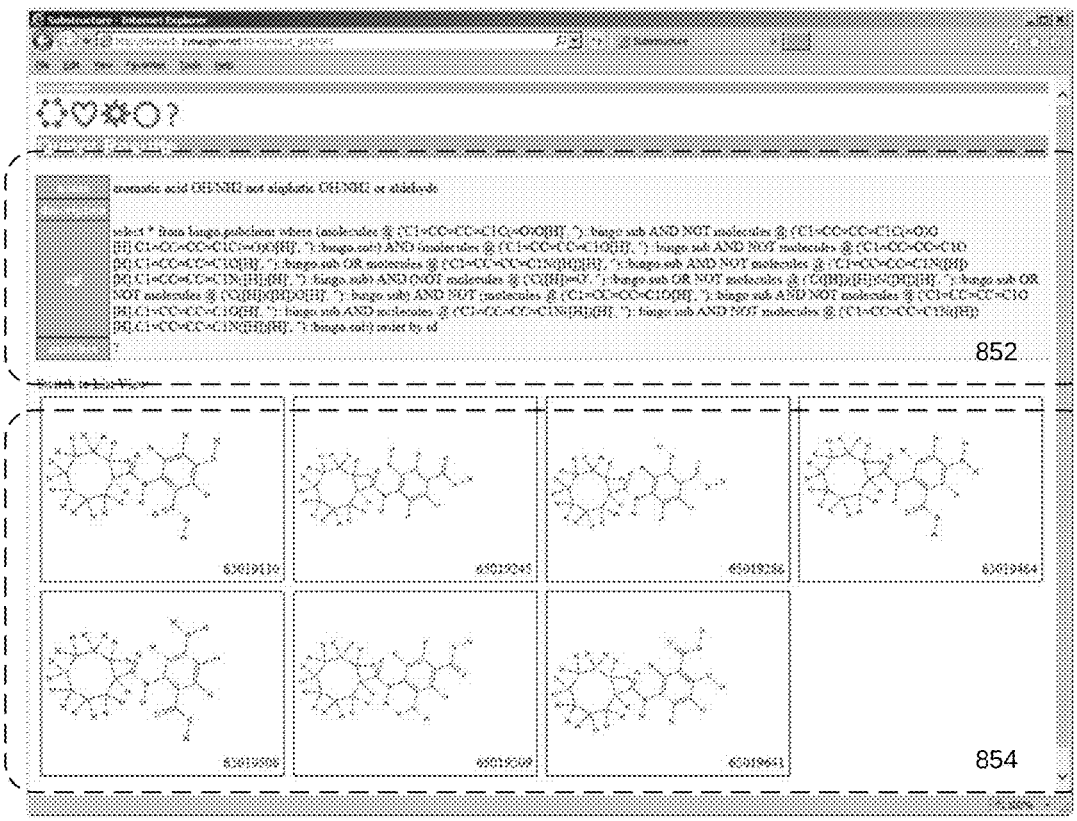
FIG. 8 illustrates a graphical user interface showing a complex query in a text-based data base query language (e.g., SQL) generated by the search engine of embodiments of the disclosure, along with graphical representations of molecules from a database that match the complex query.

The top pane of FIG. 8 shows the very complex query 852 of FIG. 7 in a text-based database query format (e.g., SQL) generated by the search engine 203 from the user's graphical substructure query entry 702 of FIG. 7. The lower portion 854 of FIG. 8 shows graphical representations of molecules from a database that match the complex query according to embodiments of the disclosure. The primary results view displays a compact grid of every matching molecule. The display flows into as much browser page space as is available, so users with large displays may be able to see a large number of molecules simultaneously. One can then see that the seven results shown are all either aromatic-acid-amines or aromatic-acid-alcohols, with various substitution patterns and additional functionality, yet none contain the excluded functional groups.

Graphical Query Retrieval

As noted above, a user may wish to reuse a previous query as a template for future queries. To that end, storage of prior query information in database tables allows the search engine 203 to retrieve stored queries. To enable retrieval, the user browses saved queries on the user interface, and selects a desired query. Then the search engine 203 retrieves all Boolean operations, molecules, and numerical constraints associated with the desired query, along with the relationships between each of them.

Next, the search engine 203 uses these lists of query components to rebuild a Boolean query tree. Using the node relationships join table, the search engine 203 constructs the logical relationships between different structure nodes.

This query tree is then fed into another translation algorithm of the search engine 203 that converts it into a set of commands that can create a visual representation of the query. These commands specify the creation of new images, user interface elements, etc. The search engine 203 sends this information to the client computer 102.

Finally, an interpreter in client 103 converts the commands into JavaScript and HTML function calls that draw the query interactively on the screen. The browser-based interpreter additionally retrieves images of drawn molecular structures by making HTTP requests to the server.

Computer System

Figure 9:
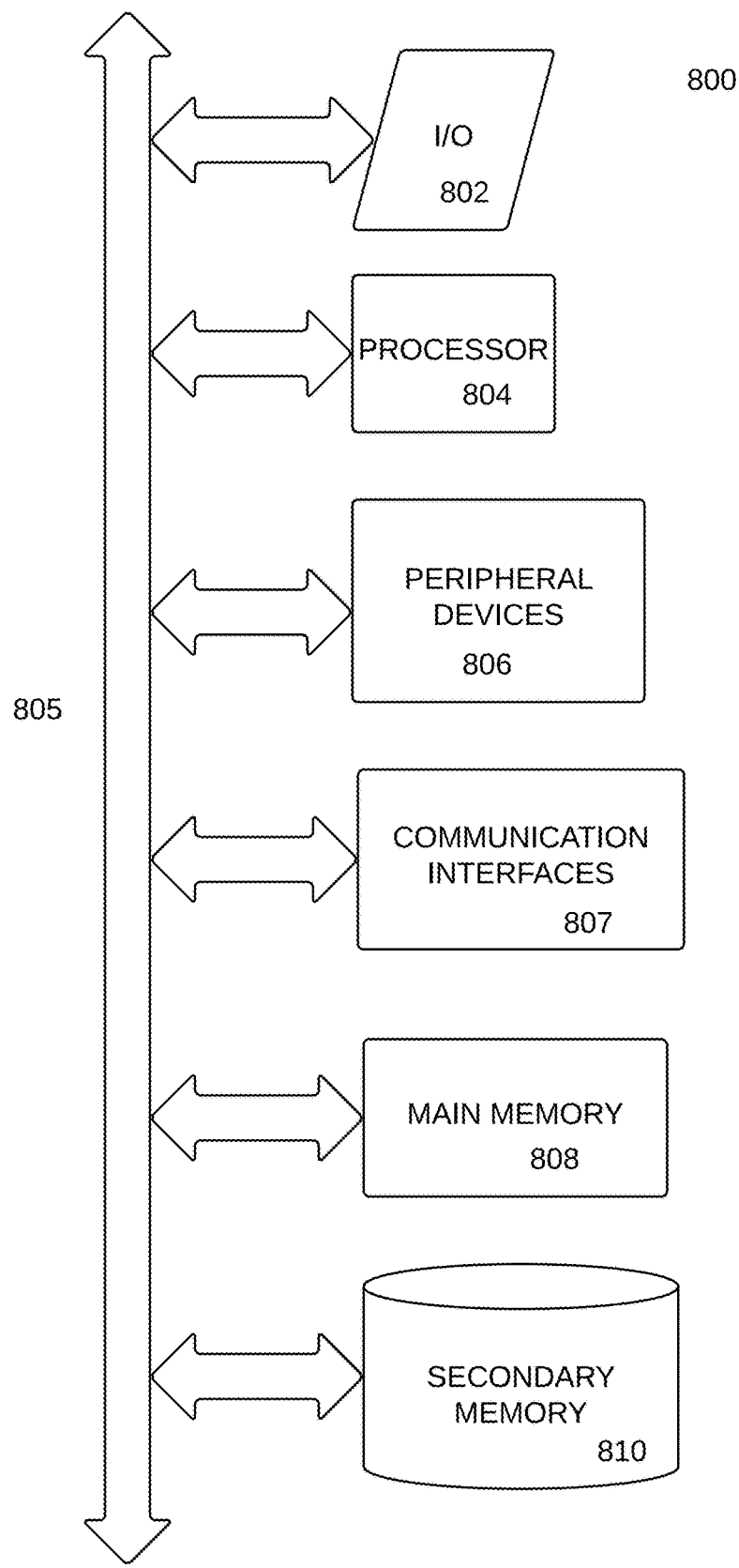
FIG. 9 illustrates an example of a computer system that may be used to execute program code stored in a non-transitory computer readable medium in accordance with embodiments of the disclosure.

FIG. 9 shows an example of a computer system 800 that may be used to execute program code stored in a non-transitory computer readable medium (e.g., memory) in accordance with embodiments of the disclosure. The computer system includes an input/output subsystem 802, which may be used to implement input interface 202 to interface with human users and/or other computer systems depending upon the application. The I/O subsystem 802 may include, e.g., a keyboard, mouse, graphical user interface, touchscreen, or other interfaces for input, and, e.g., an LED or other flat screen display, or other interfaces for output. Other elements of embodiments of the disclosure, such as the server 108, may be implemented with a computer system like that of computer system 800.

Program code may be stored in non-transitory media such as persistent storage in secondary memory 810 or main memory 808 or both. Main memory 808 may include volatile memory such as random access memory (RAM). Secondary memory may include persistent storage such as solid state drives, hard disk drives or optical disks. One or more processors 804 reads program code from one or more non-transitory media and executes the code to enable the computer system to accomplish the methods performed by the embodiments herein, such as those represented by the flow chart of FIG. 3. Those skilled in the art will understand that the processor may ingest source code, and interpret or compile the source code into machine code that is understandable at the hardware gate level of the processor(s) 804. The processor(s) 804 may communicate with external networks via one or more communications interfaces 807, such as a network interface card, WiFi transceiver, etc. A bus 805 communicatively couples the I/O subsystem 802, the processor(s) 804, peripheral devices 806, communications interfaces 807, memory 808, and persistent storage 810.

Those skilled in the art will understand that some or all of the elements of embodiments of the disclosure, such as those shown in FIGS. 1 and 2 (e.g., client computer, server search engine, data tier) and their accompanying operations, such as those shown in FIG. 3, may be implemented wholly or partially on one or more computer systems including one or more processors and one or more memory systems like those of computer system 800. Some elements and functionality may be implemented locally and others may be implemented in a distributed fashion over a network through different servers, e.g., in client-server fashion, for example. In particular, the server-side 108 operations may be made available to multiple clients in a software as a service (SaaS) fashion.

While the embodiments of the invention has been particularly described with respect to the illustrated embodiments, it will be appreciated that various alterations, modifications and adaptations may be made based on the present invention, and are intended to be within the scope of the present invention. While the invention has been described in connection with what are presently considered to be the most practical and preferred embodiments, it is to be understood that the present invention is not limited to the disclosed embodiments but, on the contrary, is intended to cover various modifications and equivalent arrangements included within the scope of the claims.

What is claimed is:

1. A computer-implemented method for providing representations of chemical compounds in response to a Boolean chemical substructure search query of at least one molecule database, the method comprising:

receiving data representing a Boolean combination of graphical representations of chemical substructures arranged in two or more rows of a graphical user interface, wherein associated with graphical representations of chemical substructures arranged in rows of the graphical user interface are logical operators representing logical combinations of a first type, associated with at least two rows of the graphical user interface is at least one logical operator representing at least one logical combination of a second type, and non-graphical chemical substructure representations correspond to the graphical representations of the chemical substructures;

for each row having graphical substructure representations associated with at least one logical operator of a first type, combining each such first-type logical operator and its associated non-graphical substructure representations into a row sub-query, wherein each logical operator is associated with at most two non-graphical substructure representations in accordance with the Boolean combination;

for each row, combining the row sub-queries into a row query in accordance with the Boolean combination;

combining the row queries with the at least one second-type logical operator in accordance with the Boolean combination to generate a composite search query;

executing the composite search query by applying the logical operators to the non-graphical substructure representations in accordance with the Boolean combination to produce Boolean query results comprising one or more chemical structures representing chemical compounds; and providing for graphical display the Boolean query results.

2. The method of claim 1, wherein if a row contains two or more two non-graphical chemical substructure representations, the row is characterized as containing one or more unique pairs of non-graphical chemical substructure representations wherein each non-graphical chemical substructure representation may be a member of only one unique pair, and combining each first-type logical operator and its associated non-graphical substructure representations into a row sub-query comprises:

combining every adjacent unique pair of non-graphical chemical substructure representations in the row with its associated first-type logical operator to form a row sub-query for each pair; and combining any single uncombined non-graphical chemical substructure representation in the row with any uncombined first-type logical operator to form a row sub-query for the uncombined non-graphical chemical substructure representation.

3. The method of claim 1, wherein each of the non-graphical representations resides in a tree data structure at an operand node that is related to at most one other operand node by a logical operator in accordance with the Boolean combination, and combining each first-type logical operator and its associated non-graphical representations into a row sub-query comprises combining each first-type logical operator and its related operand nodes into the row sub-query.

4. The method of claim 3, further comprising recursively traversing the tree data structure to generate a text-based database query to serve as the composite search query.

5. The method of claim 3, the method further comprising:

storing the operand nodes in a first database table;

storing the logical operators in a second database table; and storing relationships among the logical operators and the operand nodes in a join table, wherein executing the composite search query comprises performing database operations on the operand nodes in the first database table using the logical operators in the second database table.

6. The method of claim 5, wherein storing each operand node in a database table includes storing, for at least one operand node, an indication of the number of instances of the chemical substructure corresponding to the at least one operand node to be searched in the at least one molecule database.

7. The method of claim 1, wherein combining the row queries comprises:

combining each second-type logical operator with associated row queries to generate, for each second-type logical operator, a column sub-query, wherein each second-type logical operator is associated with at most two row queries; and combining the column sub-queries to generate the composite search query.

8. The method of claim 1, wherein the logical combinations of the first type consist of disjunctive operations, and the logical combinations of the second type consist of conjunctive operations.

9. The method of claim 1, wherein the received data further comprises data representing at least one numerical constraint indicator, each numerical constraint indicator indicating a number of instances of a corresponding chemical substructure to be searched for in the at least one molecule database.

10. A computer-implemented method for providing representations of chemical compounds in response to a Boolean chemical substructure search query of at least one molecule database, the method comprising:

receiving data representing a Boolean combination of graphical representations of chemical substructures arranged in two or more rows of a graphical user interface, wherein associated with graphical representations of chemical substructures arranged in rows of the user interface are logical operators representing logical combinations of a first type, and associated with at least two rows of the user interface is at least one logical operator representing at least one logical combination of a second type, and non-graphical chemical substructure representations correspond to the graphical representations of the chemical substructures;

traversing a tree data structure representing the Boolean chemical substructure search query to generate a text-based query, wherein the tree data structure includes a plurality of sub-query structures each comprising (a) a logical operator node representing one of the logical operators of the first type or the second type and (b) at most two child nodes, in accordance with the Boolean combination, wherein the at most two child nodes of a sub-query structure comprise one of the following sets: two operand nodes, an operand node and another sub-query structure, or two other sub-query structures, and wherein an operand node represents a non-graphical substructure representation;

executing the text-based query by applying the logical operators to the non-graphical substructure representations in accordance with the Boolean combination to produce Boolean query results comprising one or more chemical structures representing chemical compounds; and providing for graphical display the Boolean query results.

11. The method of claim 10, wherein the user interface resides at a client computing device, and a server performs the traversal of the tree data structure, the method further comprising the server translating the non-graphical representations into the operand nodes of the tree data structure.

12. The method of claim 10, wherein the user interface resides at a client computing device, and a server performs the traversal of the tree data structure, the method further comprising the client computing device translating the non-graphical representations into the operand nodes of the tree data structure.

13. The method of claim 10, further comprising:
   forming the logical operator nodes;
   forming the operand nodes;
   forming the plurality of sub-query structures from the logical operator nodes and the operand nodes; and
   generating the tree data structure from the plurality of sub-query structures.

14. A system for providing representations of chemical compounds in response to a Boolean chemical substructure search query of at least one molecule database, the system comprising:
   one or more processors; and
   one or more memories operatively coupled to at least one of the one or more processors and having instructions stored thereon that, when executed by at least one of the one or more processors, cause the system to:
      receive data representing a Boolean combination of graphical representations of chemical substructures arranged in two or more rows of a graphical user interface, wherein
         associated with graphical representations of chemical substructures arranged in rows of the graphical user interface are logical operators representing logical combinations of a first type,
         associated with at least two rows of the graphical user interface is at least one logical operator representing at least one logical combination of a second type, and
         non-graphical chemical substructure representations correspond to the graphical representations of the chemical substructures;
      for each row having graphical substructure representations associated with at least one logical operator of a first type, combine each such first-type logical operator and its associated non-graphical substructure representations into a row sub-query, wherein each logical operator is associated with at most two non-graphical substructure representations in accordance with the Boolean combination;
      for each row, combine the row sub-queries into a row query in accordance with the Boolean combination;
      combine the row queries with the at least one second-type logical operator in accordance with the Boolean combination to generate a composite search query;
      execute the composite search query by applying the logical operators to the non-graphical substructure representations in accordance with the Boolean combination to produce Boolean query results comprising one or more chemical structures representing chemical compounds; and
      provide for graphical display the Boolean query results.

15. The system of claim 14, wherein
   if a row contains two or more two non-graphical chemical substructure representations, the row is characterized as containing one or more unique pairs of non-graphical chemical substructure representations wherein each non-graphical chemical substructure representation may be a member of only one unique pair, and
   combining each first-type logical operator and its associated non-graphical substructure representations into a row sub-query comprises:
      combining every adjacent unique pair of non-graphical chemical substructure representations in the row with its associated first-type logical operator to form a row sub-query for each pair; and
      combining any single uncombined non-graphical chemical substructure representation in the row with any uncombined first-type logical operator to form a row sub-query for the uncombined non-graphical chemical substructure representation.

16. The system of claim 14, wherein
   each of the non-graphical representations resides in a tree data structure at an operand node that is related to at most one other operand node by a logical operator in accordance with the Boolean combination, and
   combining each first-type logical operator and its associated non-graphical representations into a row sub-query comprises combining each first-type logical operator and its related operand nodes into the row sub-query.

17. The system of claim 16, the one or more memories further comprising instructions stored thereon that, when executed by at least one of the one or more processors, cause the system to recursively traverse the tree data structure to generate a text-based database query to serve as the composite search query.

18. The system of claim 16, the one or more memories further comprising instructions stored thereon that, when executed by at least one of the one or more processors, cause the system to:
   store the operand nodes in a first database table;
   store the logical operators in a second database table; and
   store relationships among the logical operators and the operand nodes in a join table,
   wherein executing the composite search query comprises performing database operations on the operand nodes in the first database table using the logical operators in the second database table.

19. The system of claim 18, wherein storing each operand node in a database table includes storing, for at least one operand node, an indication of the number of instances of the chemical substructure corresponding to the at least one operand node to be searched in the at least one molecule database.

20. The system of claim 14, wherein combining the row queries comprises:
   combining each second-type logical operator with associated row queries to generate, for each second-type logical operator, a column sub-query, wherein each second-type logical operator is associated with at most two row queries; and
   combining the column sub-queries to generate the composite search query.

21. The system of claim 14, wherein the logical combinations of the first type consist of disjunctive operations, and the logical combinations of the second type consist of conjunctive operations.

22. The system of claim 14, wherein the received data further comprises data representing at least one numerical constraint indicator, each numerical constraint indicator indicating a number of instances of a corresponding chemical substructure to be searched for in the at least one molecule database.

23. A system for providing representations of chemical compounds in response to a Boolean chemical substructure search query of at least one molecule database, the system comprising:
   one or more processors; and
   one or more memories operatively coupled to at least one of the one or more processors and having instructions stored thereon that, when executed by at least one of the one or more processors, cause the system to:

receive data representing a Boolean combination of graphical representations of chemical substructures arranged in two or more rows of a graphical user interface, wherein
associated with graphical representations of chemical substructures arranged in rows of the user interface are logical operators representing logical combinations of a first type, and
associated with at least two rows of the user interface is at least one logical operator representing at least one logical combination of a second type, and
non-graphical chemical substructure representations correspond to the graphical representations of the chemical substructures;
traverse a tree data structure representing the Boolean chemical substructure search query to generate a text-based query,
wherein the tree data structure includes a plurality of sub-query structures each comprising (a) a logical operator node representing one of the logical operators of the first type or the second type and (b) at most two child nodes, in accordance with the Boolean combination,
wherein the at most two child nodes of a sub-query structure comprise one of the following sets: two operand nodes, an operand node and another sub-query structure, or two other sub-query structures, and
wherein an operand node represents a non-graphical substructure representation;
execute the text-based query by applying the logical operators to the non-graphical substructure representations in accordance with the Boolean combination to produce Boolean query results comprising one or more chemical structures representing chemical compounds; and
provide for graphical display the Boolean query results.

24. The system of claim 23, wherein the user interface resides at a client computing device, and a server comprises the one or more memories having instructions stored thereon that cause the system to:
translate the non-graphical representations into the operand nodes of the tree data structure; and
traverse the tree data structure.

25. The system of claim 23, wherein
the user interface resides at a client computing device that comprises the one or more memories having instructions stored thereon that cause the system to translate the non-graphical representations into the operand nodes of the tree data structure; and
a server comprises the one or more memories having instructions stored thereon that cause the system to traverse the tree data structure.

26. The system of claim 23, the memories further having instructions stored thereon that, when executed by at least one of the one or more processors, cause the system to:
form the logical operator nodes;
form the operand nodes;
form the plurality of sub-query structures from the logical operator nodes and the operand nodes; and
generate the tree data structure from the plurality of sub-query structures.

27. One or more non-transitory computer readable media storing instructions for providing representations of chemical compounds in response to a Boolean chemical substructure search query of at least one molecule database, wherein the instructions, when executed by one or more computing devices, cause at least one of the one or more computing devices to:
receive data representing a Boolean combination of graphical representations of chemical substructures arranged in two or more rows of a graphical user interface, wherein
associated with graphical representations of chemical substructures arranged in rows of the graphical user interface are logical operators representing logical combinations of a first type,
associated with at least two rows of the graphical user interface is at least one logical operator representing at least one logical combination of a second type, and
non-graphical chemical substructure representations correspond to the graphical representations of the chemical substructures;
for each row having graphical substructure representations associated with at least one logical operator of a first type, combine each such first-type logical operator and its associated non-graphical substructure representations into a row sub-query, wherein each logical operator is associated with at most two non-graphical substructure representations in accordance with the Boolean combination;
for each row, combine the row sub-queries into a row query in accordance with the Boolean combination;
combine the row queries with the at least one second-type logical operator in accordance with the Boolean combination to generate a composite search query;
execute the composite search query by applying the logical operators to the non-graphical substructure representations in accordance with the Boolean combination to produce Boolean query results comprising one or more chemical structures representing chemical compounds; and
provide for graphical display the Boolean query results.

28. The one or more computer-readable media of claim 27, wherein
if a row contains two or more two non-graphical chemical substructure representations, the row is characterized as containing one or more unique pairs of non-graphical chemical substructure representations wherein each non-graphical chemical substructure representation may be a member of only one unique pair, and
combining each first-type logical operator and its associated non-graphical substructure representations into a row sub-query comprises:
combining every adjacent unique pair of non-graphical chemical substructure representations in the row with its associated first-type logical operator to form a row sub-query for each pair; and
combining any single uncombined non-graphical chemical substructure representation in the row with any uncombined first-type logical operator to form a row sub-query for the uncombined non-graphical chemical substructure representation.

29. The one or more computer-readable media of claim 27, wherein
each of the non-graphical representations resides in a tree data structure at an operand node that is related to at most one other operand node by a logical operator in accordance with the Boolean combination, and
combining each first-type logical operator and its associated non-graphical representations into a row sub-query comprises combining each first-type logical operator and its related operand nodes into the row sub-query.

30. The one or more computer-readable media of claim 29, wherein the stored instructions further comprise instructions that, when executed by one or more computing devices, cause at least one of the one or more computing devices to recursively traverse the tree data structure to generate a text-based database query to serve as the composite search query.

31. The one or more computer-readable media of claim 29, wherein the stored instructions further comprise instructions that, when executed by one or more computing devices, cause at least one of the one or more computing devices to
store the operand nodes in a first database table;
store the logical operators in a second database table; and
store relationships among the logical operators and the operand nodes in a join table,
wherein executing the composite search query comprises performing database operations on the operand nodes in the first database table using the logical operators in the second database table.

32. The one or more computer-readable media of claim 31, wherein storing each operand node in a database table includes storing, for at least one operand node, an indication of the number of instances of the chemical substructure corresponding to the at least one operand node to be searched in the at least one molecule database.

33. The one or more computer-readable media of claim 27, wherein combining the row queries comprises:
combining each second-type logical operator with associated row queries to generate, for each second-type logical operator, a column sub-query, wherein each second-type logical operator is associated with at most two row queries; and
combining the column sub-queries to generate the composite search query.

34. The one or more computer-readable media of claim 27, wherein the logical combinations of the first type consist of disjunctive operations, and the logical combinations of the second type consist of conjunctive operations.

35. The one or more computer-readable media of claim 27, wherein the received data further comprises data representing at least one numerical constraint indicator, each numerical constraint indicator indicating a number of instances of a corresponding chemical substructure to be searched for in the at least one molecule database.

36. One or more non-transitory computer readable media storing instructions for providing representations of chemical compounds in response to a Boolean chemical substructure search query of at least one molecule database, wherein the instructions, when executed by one or more computing devices, cause at least one of the one or more computing devices to:
receive data representing a Boolean combination of graphical representations of chemical substructures arranged in two or more rows of a graphical user interface, wherein
associated with graphical representations of chemical substructures arranged in rows of the user interface are logical operators representing logical combinations of a first type, and
associated with at least two rows of the user interface is at least one logical operator representing at least one logical combination of a second type, and
non-graphical chemical substructure representations correspond to the graphical representations of the chemical substructures;
traverse a tree data structure representing the Boolean chemical substructure search query to generate a text-based query,
wherein the tree data structure includes a plurality of sub-query structures each comprising (a) a logical operator node representing one of the logical operators of the first type or the second type and (b) at most two child nodes, in accordance with the Boolean combination,
wherein the at most two child nodes of a sub-query structure comprise one of the following sets: two operand nodes, an operand node and another sub-query structure, or two other sub-query structures, and
wherein an operand node represents a non-graphical substructure representation;
execute the text-based query by applying the logical operators to the non-graphical substructure representations in accordance with the Boolean combination to produce Boolean query results comprising one or more chemical structures representing chemical compounds; and
provide for graphical display the Boolean query results.

37. The one or more computer readable media of claim 36, wherein the user interface resides at a client computing device, and a server comprises at least one of the one or more computing devices that:
translate the non-graphical representations into the operand nodes of the tree data structure; and
traverse the tree data structure.

38. The one or more computer readable media of claim 36, wherein
the user interface resides at a client computing device that comprises at least one of the one or more computing devices that translate the non-graphical representations into the operand nodes of the tree data structure; and
a server comprises at least one of the one or more computing devices that traverse the tree data structure.

39. The one or more computer readable media of claim 36, wherein the one or more non-transitory computer readable media further store instructions that, when executed by one or more computing devices, cause at least one of the one or more computing devices to:
form the logical operator nodes;
form the operand nodes;
form the plurality of sub-query structures from the logical operator nodes and the operand nodes; and
generate the tree data structure from the plurality of sub-query structures.

* * * * *

UNITED STATES PATENT AND TRADEMARK OFFICE
CERTIFICATE OF CORRECTION

PATENT NO. : 10,318,526 B2  
APPLICATION NO. : 15/202439  
DATED : June 11, 2019  
INVENTOR(S) : Erik Jedediah Dean, Adam Safir and Gregory Michael Werner Page 1 of 1

It is certified that error appears in the above-identified patent and that said Letters Patent is hereby corrected as shown below:

On the Title Page

Item (72) Inventor name "Erik Jededian Dean" should read --Erik Jedediah Dean--.

Signed and Sealed this  
Second Day of June, 2020

Andrei Iancu  
*Director of the United States Patent and Trademark Office*